(12) United States Patent
Yokoi

(10) Patent No.: US 11,291,416 B2
(45) Date of Patent: Apr. 5, 2022

(54) PARAMETER ESTIMATION METHOD AND X-RAY CT SYSTEM

(71) Applicant: HITACHI, LTD., Tokyo (JP)

(72) Inventor: Kazuma Yokoi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 51 days.

(21) Appl. No.: 16/636,404

(22) PCT Filed: Jun. 7, 2018

(86) PCT No.: PCT/JP2018/021911
§ 371 (c)(1),
(2) Date: Feb. 4, 2020

(87) PCT Pub. No.: WO2019/031045
PCT Pub. Date: Feb. 14, 2019

(65) Prior Publication Data
US 2020/0245956 A1    Aug. 6, 2020

(30) Foreign Application Priority Data
Aug. 10, 2017 (JP) .............................. JP2017-155232

(51) Int. Cl.
*A61B 6/03* (2006.01)
*A61B 6/00* (2006.01)
*G06T 11/00* (2006.01)

(52) U.S. Cl.
CPC .............. *A61B 6/03* (2013.01); *A61B 6/4241* (2013.01); *A61B 6/5211* (2013.01);
(Continued)

(58) Field of Classification Search
CPC ......... A61B 6/03; A61B 6/032; A61B 6/4241; A61B 6/483; A61B 6/5211; A61B 6/5217; G06T 11/006
See application file for complete search history.

(56) References Cited

U.S. PATENT DOCUMENTS 5,680,471 A * 10/1997 Kanebako ............. G06T 7/0012
  382/128
2002/0072665 A1* 6/2002 Ozaki .................. A61B 6/5217
  600/408

(Continued)

FOREIGN PATENT DOCUMENTS

JP    2015-525360 A    9/2015
JP    2017-136342 A    8/2017
WO   2016/158234 A1   10/2016

OTHER PUBLICATIONS

Vinicius C. Assis, et al., "Double Noise Filtering in CT: Pre- and Post-Reconstruction", 2015 28th SIBGRAPI Conference on Graphics, Patterns and Images, Salvador. Proceedings. Los Alamitos: IEEE Computer Society's Conference Publishing Services, 2015. On-line.

(Continued)

*Primary Examiner* — Dani Fox
*Assistant Examiner* — Soorena Kefayati
(74) *Attorney, Agent, or Firm* — Mattingly & Malur, PC

(57) ABSTRACT

An X-ray CT device and a computing unit to use a projection-based method for image reconstruction are included. The computing unit sets a coordinate space having coordinate axes of the thicknesses of base materials and likelihood the thicknesses, and then based on X-ray attenuation responses, executes: a first search to search in a direction perpendicular to a ridge direction of likelihood contours for a first estimated thickness having the highest likelihood, starting with an estimated thickness input value set in the coordinate space; a second search to search for a second estimated thickness having the highest likelihood, starting with a shifted starting point at a position shifted from the estimated thickness input value; and a third search to search on a line connecting the first estimated thickness with the (Continued)

second estimated thickness for the highest likelihood estimator having the highest likelihood, to obtain an estimated thickness output value.

4 Claims, 5 Drawing Sheets

(52) U.S. Cl.
CPC .......... *A61B 6/5217* (2013.01); *G06T 11/006* (2013.01); *A61B 6/032* (2013.01); *A61B 6/482* (2013.01)

(56) References Cited

U.S. PATENT DOCUMENTS

| | | | |
|---|---|---|---|
| 2002/0186872 A1* | 12/2002 | Avinash | A61B 6/00 382/132 |
| 2005/0135664 A1* | 6/2005 | Kaufhold | G06T 11/006 382/131 |
| 2006/0109949 A1 | 5/2006 | Tkaczyk et al. | |
| 2008/0042067 A1* | 2/2008 | Rousso | G01T 1/161 250/363.04 |
| 2008/0135789 A1 | 6/2008 | Du et al. | |
| 2010/0166281 A1* | 7/2010 | Burger | A61B 6/507 382/131 |
| 2011/0164031 A1* | 7/2011 | Shi | G06T 11/006 345/419 |
| 2011/0164798 A1* | 7/2011 | Masumoto | A61B 5/1075 382/131 |
| 2012/0089016 A1* | 4/2012 | Mizuno | G06T 7/20 600/425 |
| 2012/0271162 A1* | 10/2012 | Liao | G06T 7/20 600/424 |
| 2014/0010431 A1* | 1/2014 | Stayman | G06T 11/006 382/131 |
| 2014/0236488 A1* | 8/2014 | Brown | A61B 6/4241 702/19 |
| 2015/0177395 A1* | 6/2015 | Proksa | A61B 6/4241 702/104 |
| 2015/0248593 A1* | 9/2015 | Nakashima | A61B 6/5217 382/131 |
| 2016/0174902 A1* | 6/2016 | Georgescu | G06T 7/0012 600/408 |
| 2016/0275679 A1* | 9/2016 | Im | A61B 6/14 |
| 2016/0363442 A1* | 12/2016 | Brambilla | G01B 15/02 |
| 2016/0363545 A1* | 12/2016 | Gorecki | G01N 23/087 |
| 2017/0046839 A1* | 2/2017 | Paik | G06K 9/00147 |
| 2017/0076014 A1* | 3/2017 | Bressloff | A61B 6/504 |
| 2017/0206681 A1* | 7/2017 | Choi | A61B 6/5205 |
| 2017/0224299 A1* | 8/2017 | Petschke | A61B 6/032 |
| 2017/0270687 A1* | 9/2017 | Manhart | G06T 11/008 |
| 2017/0296137 A1* | 10/2017 | West | G06T 11/008 |
| 2017/0303869 A1* | 10/2017 | Goshen | A61B 6/463 |
| 2018/0012356 A1* | 1/2018 | Madabhushi | G06K 9/6267 |
| 2018/0061097 A1 | 3/2018 | Yokoi et al. | |
| 2018/0116621 A1* | 5/2018 | Berker | A61B 6/5247 |
| 2018/0271375 A1* | 9/2018 | Dharmakumar | A61B 5/7207 |
| 2019/0021677 A1* | 1/2019 | Grbic | A61B 5/7292 |
| 2019/0046127 A1* | 2/2019 | Furukawa | A61B 6/03 |
| 2019/0162679 A1* | 5/2019 | Yamakawa | G01N 23/087 |
| 2019/0172197 A1* | 6/2019 | Buckler | G06T 5/003 |
| 2019/0188898 A1* | 6/2019 | Sekiguchi | G06T 3/4007 |
| 2019/0213715 A1* | 7/2019 | Li | A61B 6/482 |
| 2020/0005942 A1* | 1/2020 | Kawagishi | G06T 7/0016 |

OTHER PUBLICATIONS

Ewald Roessl, et al., "A comparative study of a dual-energy-like imaging technique based on counting-integrating readout," Medical Physics, Nov. 10, 2011, vol. 38(12), p. 6416-6428.

International Search Report of PCT/JP2018/021911 dated Aug. 28, 2018.

* cited by examiner

PARAMETER ESTIMATION METHOD AND X-RAY CT SYSTEM

TECHNICAL FIELD

The present invention relates to a technique of parameter estimation method and an X-ray CT system.

BACKGROUND ART

An X-ray CT (Computer Tomography) imaging device (hereinafter referred to as an X-ray CT device as appropriate) is generally configured to use a current mode X-ray detector, which is unable to obtain energy information, for detecting X-ray photon groups having continuous (non-monochromatic) energy distribution by an X-ray tube (X-ray energy distribution: hereinafter referred to as a spectrum). Incidentally, the X-ray attenuation coefficient has a specific energy dependency for each atomic number. Therefore, information on atomic numbers is acquirable from attenuation coefficients in different spectra. However, the current mode X-ray detector is unable to obtain energy information and accordingly unable to obtain information on atomic numbers.

There are mainly two techniques to effectively use information from X-rays having spectra, as follows. The first one is Dual Energy CT. This technique uses two continuous spectra from two types of X-ray tube voltages, with the detector in current mode. The second one is a technique called photo counting CT (PCCT), spectral CT, or the like. This technique uses a pulse mode detector, which is able to obtain energy information.

The X-ray CT device is used to inspect differences in abilities of substances to block X-rays (attenuation coefficients). However, the dependency of the X-ray attenuation coefficient on energy differs for each element (atomic number). This property is utilized when an N number of types of energy information are obtained, to break down materials using an arbitrary M (M≤N) number of materials, having different effective atomic numbers, as base materials (see Patent Document 1, for example). There are two image reconstruction methods: a projection-based method (pre-reconstruction method) and an image-based method (post-reconstruction method), depending on whether the material breakdown is executed before or after reconstructing an image from projection data (at the time of image reconstruction) (see Non-Patent Document 1, for example). The PCCT uses smaller detection elements than a conventional X-ray CT because of high flux conditions in a clinical CT. The projection-based method is generally used to handle such a complex spectrum response.

PRIOR ART DOCUMENTS

Patent Documents

Patent Document 1: U.S. Patent Application Publication No. 2006/0109949

Non-Patent Documents

ASSIS, V. C.; SALVADEO, D. H. P.; MASCARENHAS, N. D. A.; LEVADA, A. L. M. "Double Noise Filtering in CT: Pre- and Post-Reconstruction," 2015 28th SIBGRAPI Conference on Graphics, Patterns and Images, Salvador. Proceedings. Los Alamitos: IEEE Computer Society's Conference Publishing Services, 2015. On-line

SUMMARY OF THE INVENTION

Problems to be Solved

In general, the image reconstruction method based on the projection-based method estimates the highest likelihood of the thickness of the base material for the likelihood obtained from two spectra: the measured spectrum and the assumed spectrum (average spectrum) corresponding to the estimated thickness of the base material. Note that the "average" of the average spectrum is an expected value of the count corresponding to the thickness of the base material (i.e., examined in the past). The assumed spectrum is a spectrum assumed to be an average value based on past data for the thickness of a certain base material. The highest likelihood estimator of the thickness of the base material is calculable based on the thickness of the base material and the assumed spectrum (average spectrum). However, calculating the highest likelihood estimator of the thickness of the base material based on the assumed spectrum (average spectrum) generally involves a high calculation load (details will be described below).

In addition, there are multiple search methods for the highest likelihood estimation, and the highest likelihood estimator is generally obtained through iterative calculations in such highest likelihood estimation. However, the search method may have a problem that the number of repeated calculations increases to have the increased calculation load.

The present invention has been made in view of such a background to achieve efficient estimation and search of parameters.

Solution to Problems

The present invention can solve the above-described problem, and provides a method for a computing unit applying a projection-based method to X-ray attenuation responses through an imaged subject, having X-ray energy distribution for an N (N≥2) number of first parameters, to reconstruct an image using estimated values on given values in the responses for an M (M≤N) number of second parameters, the method including: setting a coordinate space to have coordinate axes of the M number of second parameters and likelihood of the M number of second parameters; executing a first step of setting a predetermined starting point in the coordinate space based on the X-ray attenuation response, and doing a first search to search in a predetermined direction in the coordinate space from the starting point for a first value to have the highest likelihood; executing a second step of doing a second search to search for a second value to have the highest likelihood, under the condition that at least one of a starting point and a direction for the second search is different from that for the first search; and executing a third step of doing a third search to search on a line connecting the first value with the second value for a highest likelihood estimator to have the highest likelihood, and setting the highest likelihood estimator as an estimated value by the M number of second parameters. Other solutions are to be described as appropriate in the embodiments.

Advantageous Effects of the Invention

The present invention achieves efficient estimation and search of parameters.

DETAILED DESCRIPTION OF THE EMBODIMENT

Next, embodiments of the present invention will be described in detail with reference to the drawings as appropriate.

<X-Ray CT System 10>

Figure 1:
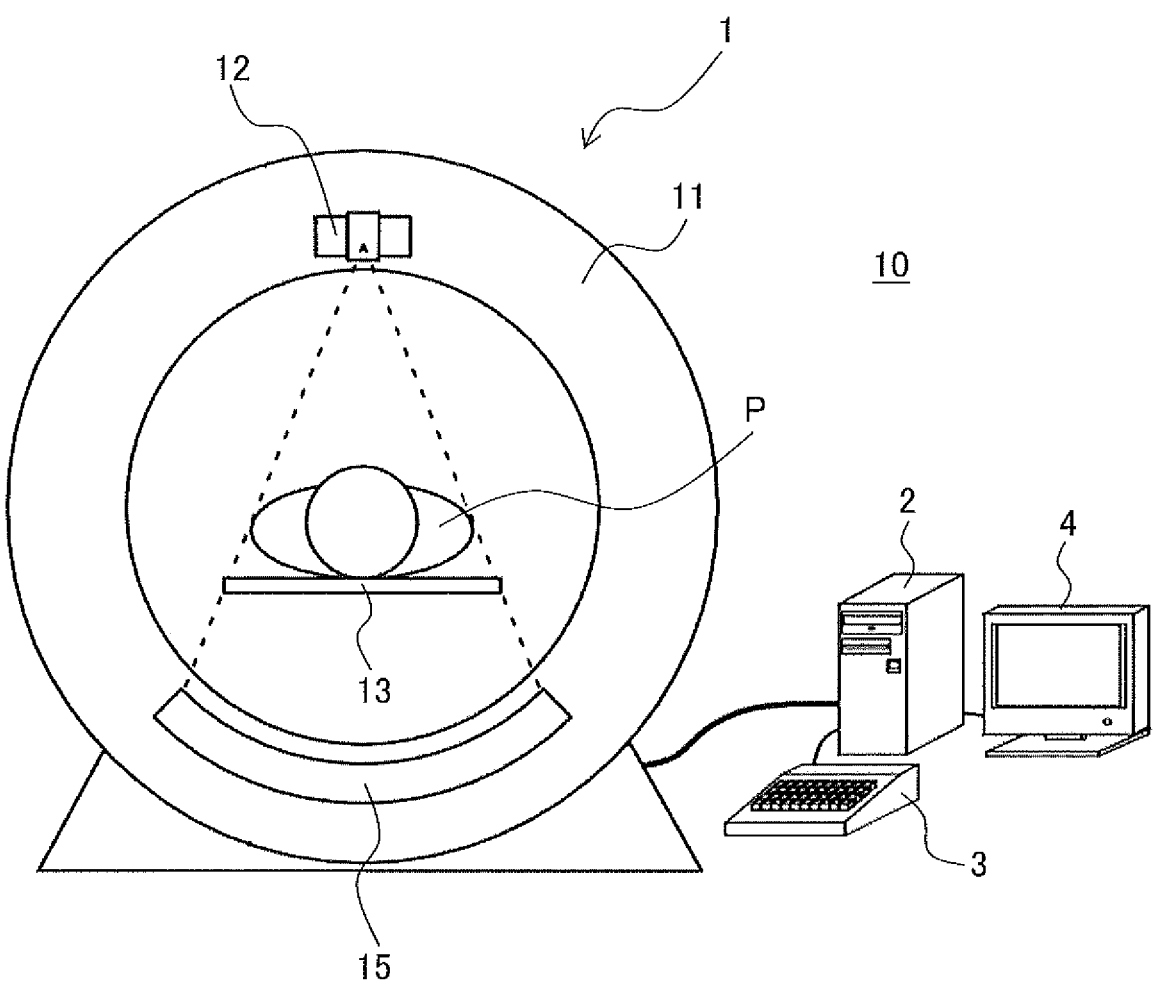
FIG. 1 is a schematic diagram of an X-ray CT system 10 according to a first embodiment.

FIG. 1 is a schematic diagram of an X-ray CT system 10 according to a first embodiment. The X-ray CT system 10 includes an X-ray CT device 1, a computing device 2 such as a PC (Personal Computer), an input device 3, and a display device 4. The X-ray CT device 1 includes a gantry 11, an X-ray tube 12, a bed 13, and an X-ray detector 15. A subject P to be imaged is stationary on the bed 13. The X-ray tube 12 and the X-ray detector 15 are arranged to face each other across the subject P being stationary on the bed 13. In response to operation information inputted from the input device 3, a rotation driver (not shown) of the gantry 11 rotates a set of the X-ray tube 12 and the X-ray detector 15 around the body axis of the subject P. At this time, X-rays radiated from the X-ray tube 12 and attenuated by the subject P are measured by the X-ray detector 15.

Here, the X-ray detector 15 is assumed to operate in pulse mode in which energy information is acquirable. The X-ray detector 15 obtains count (that is, spectrum) information for an N number of types of energy. Then, the computing device 2 executes an image reconstruction process on the spectrum information detected for each projection path (rotational angle position, detector position) of the obtained sinogram. The display device 4 then displays the tomogram as a computed result.

<Computing Device 2>

Figure 2:
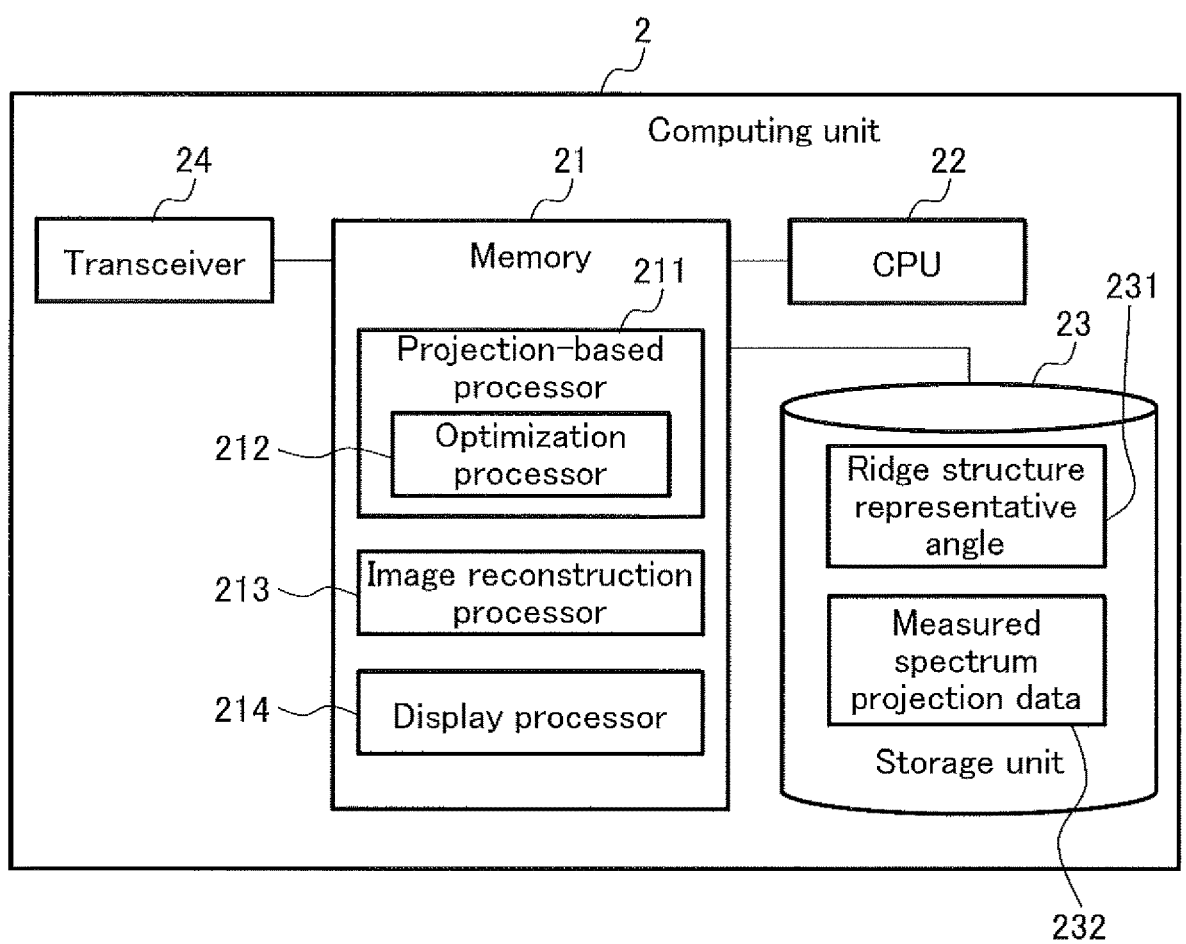
FIG. 2 is a functional block diagram to show exemplary configuration of a computing device 2 used in the present embodiment.

FIG. 2 is a functional block diagram to show an exemplary configuration of the computing device 2 used in the present embodiment. The computing device 2 includes a memory 21, a CPU (Central Processing Unit) 22, a storage unit 23 such as an HD (Hard Disk), and a transceiver 24. A program is loaded into the memory 21 from the storage unit 23. Then, the program loaded into the memory 21 is executed by the CPU 22 to embody a projection-based processor 211, an image reconstruction processor 213, and a display processor 214.

The projection-based processor 211 executes a material breakdown process by the projection-based method. The projection-based processor 211 has an optimization processor 212. The optimization processor 212 executes an optimization process to be described below. The image reconstruction processor 213 executes an image reconstruction process on the data subjected to the material breakdown process by the projection-based processor 211. The display processor 214 displays the result of the image reconstruction process on the display device 4 (see FIG. 1).

The storage unit 23 stores a ridge structure representative angle 231 and measured spectrum projection data 232. The ridge representative angle is to be described below. The measured spectrum projection data 232 here is data (spectrum) imaged by the X-ray CT device 1. The transceiver 24 transmits/receives data to/from the X-ray CT device 1 or the like.

<Overall Process>

Figure 3:
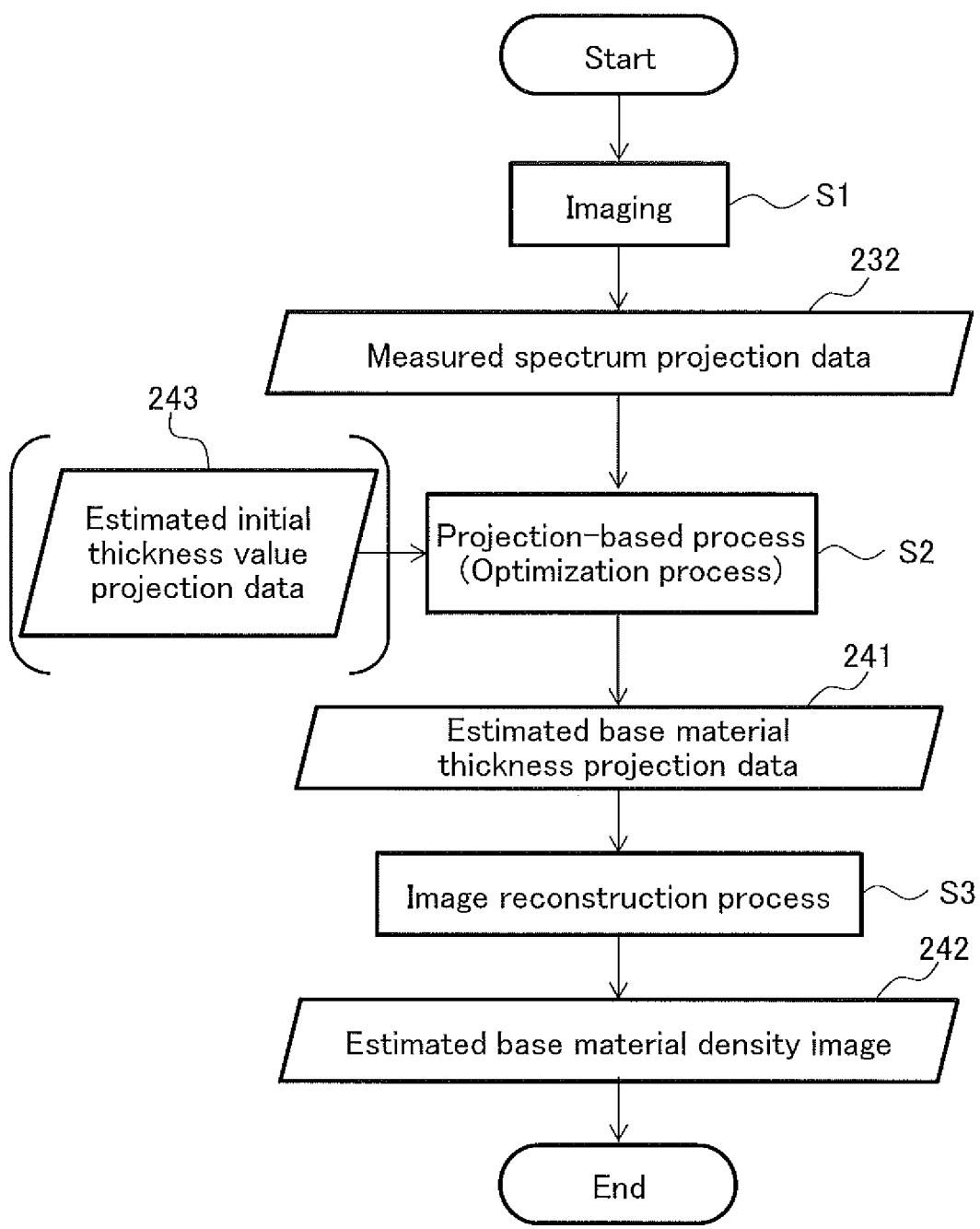
FIG. 3 is a flowchart to show a CT image reconstruction process of the present embodiment.

FIG. 3 is a flowchart to show the CT image reconstruction process executed in the present embodiment. FIGS. 1 and 2 are referenced as appropriate. Note that the processes in FIG. 3, other than the optimization process (S2), are generally executed ones, and thus detailed descriptions thereof are dispensed with. First, the X-ray CT device 1 executes imaging on the subject P (S1). As a result of this imaging, the measured spectrum projection data 232 is obtained for each projection path in the sinogram.

Next, the projection-based processor 211 executes the projection-based process (S2). Note that the optimization processor 212 executes the optimization process during the projection-based process. The optimization process is to be described below, with reference to FIGS. 4 and 5.

It is ideally desirable that in an energy window of a certain projection path, only those X-rays, which have come incident on the subject P through said projection path with said energy and then are attenuated, are counted. However, X-rays through different projection paths with different energy from those of the X-rays, which have come incident on the subject P, may cumulatively be counted in reality, due to scattering in the subject P, scattering in the X-ray detector 15, and the like. The measured spectrum projection data 232 is obtained as a result of such complicated spectrum responses. However, if the responses are acquired in advance for the thicknesses of arbitrary materials selected as base materials, the probability of the measured spectrum projection data 232 being reached for the combination of the thicknesses (parameters) of the base materials is calculated. Note that this probability is counted as the likelihood using the basis materials as parameters. That is, for the combination of the thicknesses of the base materials, the probability of the measured spectrum projection data 232, which has been taken this time, being reached has the same numerical value as the likelihood using the base materials as parameters.

The known information on the correspondence between the combination of the base material thicknesses and the assumed (average) spectrum may be a computer simulation result of X-ray behavior, actual measurements by the X-ray detector 15, or a combination thereof. At this time, a method of obtaining a combination of base material thicknesses having the highest likelihood (estimated base material thickness projection data 241) for each projection path is the projection-based method. The projection-based method generally requires no specific initial values and starts with an appropriate default value. For example, an image having a uniform pixel value is used as the initial value. However, if a value close to the solution is known by some other method, this value may be used as estimated initial thickness value projection data 243. The estimated initial thickness value projection data 243 is created based on projection data estimated to be obtained when a simple cylinder is imaged, or the like, for example.

After the projection-based process, the image reconstruction processor 213 executes an image reconstruction process (S3) using the estimated base material thickness projection data (estimated parameter) 241 outputted as a result of the projection-based process. The image reconstruction processor 213 converts the estimated base material thickness projection data 241 into an estimated base material density image 242 by an image reconstruction method such as FBP (Filtered Back Projection).

<Optimization Process>

Figure 4:
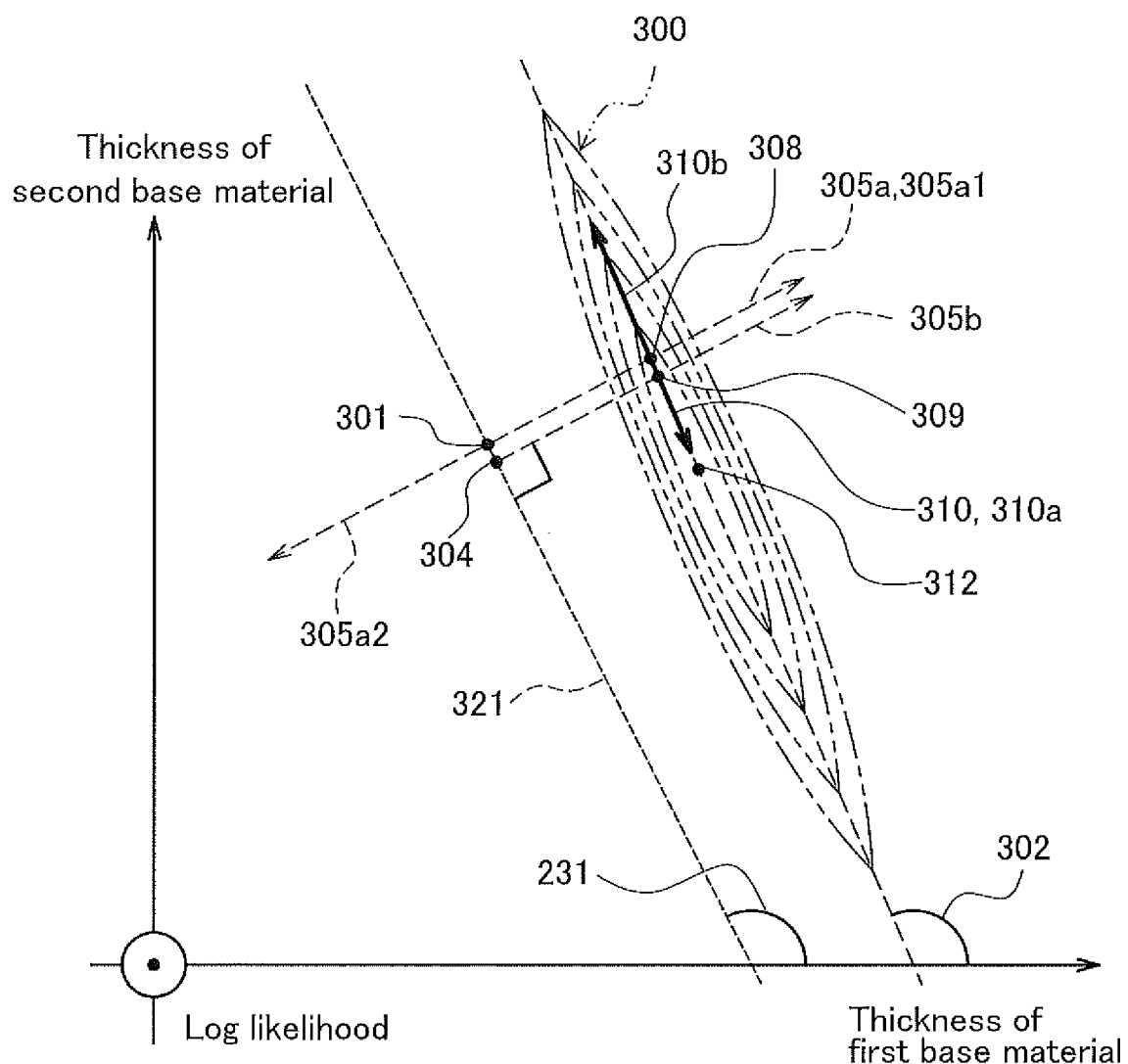
FIG. 4 is a chart to show an optimization technique used in the present embodiment.
Figure 5:
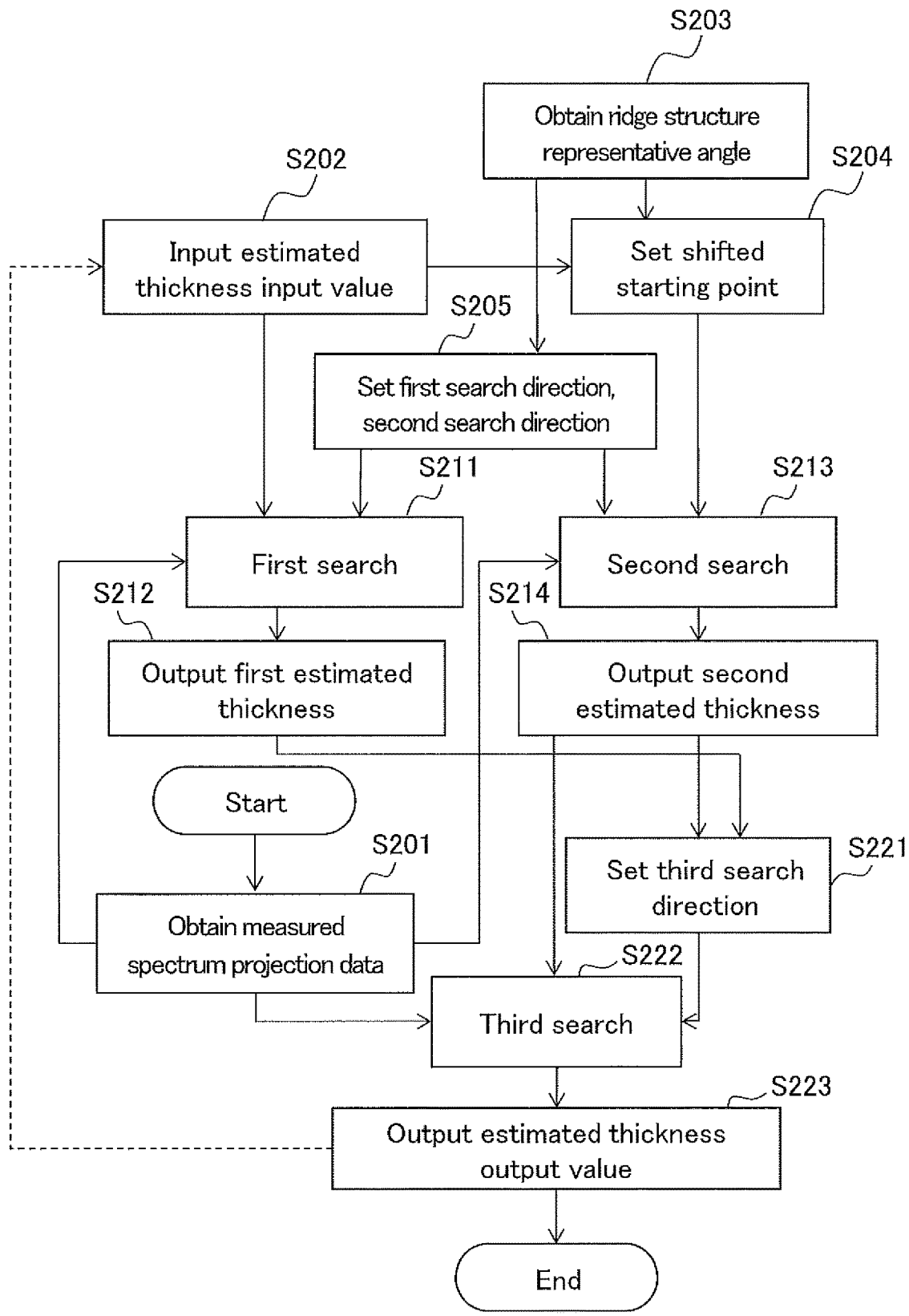
FIG. 5 is a flowchart to show a procedure of the optimization technique used in the present embodiment.

FIG. 4 is a chart to show an optimization technique used in the present embodiment. FIG. 5 is a flowchart to show the procedure of the optimization technique used in the present embodiment. Here, a description is to be given mainly with reference to FIG. 4, and with reference to FIG. 5 as required. Note that step numbers in this description indicate those in FIG. 5. Here, for the sake of simplification, it is assumed that the thickness is independently estimated for each projection path. Likelihood contours (evaluation function) 300 show distribution of the likelihood of the thicknesses of base materials when there are two base materials. Note that the number of base materials is two in the present embodiment, but may be three or more. In this case, coordinate axes corresponding to the number of base materials are set in the coordinate space in FIG. 4. In the coordinate space in FIG. 4, the direction perpendicular to the plane of paper is a coordinate axis of the likelihood.

Here, there is no specific limitation in the projection-based method about how to obtain the highest likelihood. In a very primitive way, the likelihood may be comprehensively examined for each combination of the thicknesses of the basis materials to select the point indicating the highest likelihood. That is, the likelihood may be examined for all combinations of the thicknesses of the base materials in the coordinate space (all possible coordinate values in the coordinate space) in FIG. 4. However, if the step size for the combination is made finer, the number of calculations increases with the power of the number of coordinate axes, and this technique is not realistic. The power of the number of coordinate axes means $n^3$ if there are three coordinate axes, for example. Here, "n" is the number of steps for the combination.

Then, various obtaining-the-highest (optimization) techniques devised to efficiently reach the peak are generally used to obtain an optimum value. Popular optimization techniques include a steepest descent method to obtain a gradient direction for each candidate point and repeat a line search, and a conjugate gradient method to repeat a line search in a direction conjugate with a past search vector. However, the steepest descent method is known to have a very large number of iterations at elongated trough portions (ridge in the case of obtaining-the-highest approach) of the evaluation function. With the conjugate gradient method, the number of iterations is converged for quadratic functions with the minimum number of times even at the trough or ridge structure of the evaluation function, but such convergence is not guaranteed for non-quadratic functions. The present embodiment proposes a new optimization method in the X-ray CT art field for acquiring energy information, focusing on the fact that the distribution of the likelihood on the measured spectrum projection data 232, using the thicknesses of base materials as parameters, has a ridge structure and is not necessarily defined by a quadratic function.

First, the optimization processor 212 sets a coordinate space having the respective thicknesses of base materials and the likelihood (log likelihood) as coordinate axes, as shown in FIG. 4. Regarding the coordinate axes in the example in FIG. 4, the horizontal axis indicates the thickness of a first base material. The vertical axis indicates the thickness of a second base material. The direction perpendicular to the plane of paper indicates the likelihood. The first base material is water, for example, and the second base material is bone, for example. Here, the log likelihood is monotonously increased with respect to the increase in the likelihood, and thus the position of a combination of the thicknesses having the highest likelihood is the same as that having the highest log likelihood. That is, the result is the same whether the likelihood is estimated using the log likelihood or the likelihood other than the log likelihood. In the present embodiment, the log likelihood is used as a substitute for the likelihood in order to save the number of digits.

As shown in FIG. 4, the estimated likelihood contours 300 are estimated to have distribution having a ridge in an elongated straight shape. Note that the likelihood contours 300 are actually unknown, but are presumed, from experience, to have a geometry shown by phantom lines in FIG. 4. Additionally, the ridge structure of the likelihood contours 300 is known not to be defined by a quadratic function. Then, a ridge search method to be described below is used as an optimization method used when optimization by the conjugate gradient method is not suitable.

The ridge search method is an optimization method to find two points on the ridge through two initial line searches (hereinafter referred to as searches) and then to execute a third search on an extension of a line connecting the two points with each other.

First, the optimization processor 212 obtains the measured spectrum projection data 232 from the storage unit 23 (S201). Here, the obtained measured spectrum projection data 232 is the result of the current imaging. That is, the data is the result obtained by imaging in step S1 in FIG. 3.

Next, an estimated thickness input value (predetermined parameter) 301 is inputted based on the measured spectrum projection data 232 (S202). As described above, the estimated thickness input value 301 may be an image with uniform pixel values, the estimated initial thickness value projection data 243 as described above, a value close to the solution by some other method, or a value of the last-calculated highest likelihood estimator used as next input data in a step-by-step manner.

The optimization processor 212 obtains the ridge structure representative angle 231, which is the same angle as an actual ridge structure angle 302, from the storage unit 23 (S203). The ridge structure representative angle 231 is stored in the storage unit 23 in advance. Here, when the X-ray energy is monochromatic, the actual ridge structure angle 302 is a value determined by the ratio between the X-ray attenuation coefficients of the base materials in the X-ray energy. The actual ridge structure angle 302 is set here to an angle formed by the coordinate axis of the thickness of the first base material and the ridge of the likelihood contours 300.

The X-ray CT actually uses polychromatic X-rays (X-rays including a plurality of wavelengths). Besides, the remaining count after attenuation is different for every energy, and thus the actual ridge structure angle 302 is not fixed unless the combination of the thicknesses of the base materials is determined first. However, the rough actual ridge structure angle 302 has a close value in a wide range of base material thicknesses. That is, the actual ridge structure angle 302 is almost the same at any location in the coordinate space in FIG. 4.

Note that the actual ridge structure angle 302 is unknown until the end of the optimization process, but an approximate angle is known from past experiences. That is, the actual ridge structure angle 302 (the ridge orientation of the likelihood contours 300) is known, but it is unknown where the ridge of the likelihood contours 300 exists in the coordinate space. Next, the optimization processor 212 sets a ridge structure representative line 321, which forms an angle of the ridge structure representative angle 231 with the coordinate axis of the thickness of the first base material (i.e., parallel to the ridge of the likelihood contours 300) and runs through the estimated thickness input value 301.

Then, the optimization processor 212 sets a shifted starting point 304, different from the estimated thickness input value 301, on the ridge structure representative line 321 (S204).

In addition, the optimization processor 212 sets a first search direction 305a and a second search direction 305b based on the ridge structure representative angle 231 (S205). As shown in FIG. 4, the first search direction 305a and the second search direction 305b are perpendicular to the ridge structure representative line 321. Here, the first search direction 305a is a direction in which a first search to be described below is executed. Likewise, the second search direction 305b is a direction in which a second search to be described below is executed.

Searching in the ridge search method used in the present embodiment requires a starting point and a search direction. As described above, the estimated thickness input value 301 is the starting point of the first search. Note that there are two directions which are perpendicular to the ridge structure representative line 321 (directions indicated by reference numerals 305a1 and 305a2 in FIG. 4). Therefore, the optimization processor 212 obtains a likelihood gradient in each direction as required and selects a direction in which the likelihood increases. Additionally, there is no common optimum value for the initial movement distance (search vector length) for the first search, and thus a predetermined fixed value shall be used, or the user shall suitably select the value depending on the system.

Next, the optimization processor 212 executes the first search to search in the first search direction 305a for a point where the likelihood (log likelihood) becomes the highest (first estimated thickness 308), with the estimated thickness input value 301 as a starting point (S211). The "thickness" here is the thickness of the base material. Note that the first search may be executed before the shifted starting point 304 is set.

As a result, the first estimated thickness (first value) 308 is obtained. In the example in FIG. 4, the first estimated thickness 308 is a combination of the thickness of the first base material and the thickness of the second base material. In the first search, the likelihood may be obtained in the first search direction 305a for every fixed point. Alternatively, the optimization processor 212 may set points for search with point-to-point distance of 1, 2, 4, and so on, respectively, until reaching a point where the obtained likelihood is lower than the likelihood obtained at the prior point, and then execute a detailed search between the prior point and the current point. Here, assuming that the likelihood at the first estimated thickness 308 is T, T is expressed by the following Equation (1).

$$T = \underset{TM}{\mathrm{argmax}} L(Cest(TM) \mid Cobs(EN)) \quad (1)$$
$$= \underset{TM}{\mathrm{argmax}} \left( \sum_{Cobs(Ei)} \ln f(Cest(TM) \mid Cobs(Ei)) \right).$$

Here, TM is the thicknesses of an M number of base materials (M number of second parameters). That is, TM= (T1, T2, - - -, TM). In the example in FIG. 4 to be described below, TM=(T1, T2). Here, T1 is the thickness of the first base material, and T2 is the thickness of the second base material. Cobs (EN) is the measured spectrum having an N number of energy (N number of first parameters) imaged this time. That is, EN=(E1, E2, - - -, EN). TM is a parameter known from EN (TM is a parameter included in EN). Cest (TM) is an estimated spectrum when the thicknesses of the base materials are TM=(T1, T2, - - -, TM). Cest (TM) is known based on past data. f(Ccest (TM)|Cobs (Ei)) is the probability of TM occurring in unit time under Cobs (Ei). Note that this probability assumes a Poisson distribution. Here, TM is a variable, and EN is a fixed value (hence, Cobs (EN) is also a fixed value). In the first search, the optimization processor 212 changes the value of TM in the first search direction 305a, with the estimated thickness input value 301 as a starting point, and sets TM, with which the likelihood L (·) indicated in Equation (1) becomes the highest, to T. Intuitively, what is obtained is TM having the highest probability of the thicknesses TM of the M number of base materials occurring, under the condition that the imaged measured spectrum projection data 232 has been generated. That is, Equation (1) obtains TM (a combination of (T1, T2, - - -, TM)) which highly likely (with high probability) acquires EN obtained by the current imaging.

As described above, searching by the ridge search method requires the measured spectrum projection data 232, which is measurement data of the subject P. The measured spectrum projection data 232 is also used for calculating the likelihood contours, from which the likelihood to be used in the search is calculated.

As described above, the optimization processor 212, under the condition that the ridge structure representative angle 231 is prepared in advance, executes the first search in a direction perpendicular to the ridge structure representative angle 231. In this way, the first search is executed substantially perpendicularly to the actual ridge structure angle 302. That is, the optimization processor 212 reaches the first estimated thickness 308, which is a point on the ridge of the likelihood contours 300, with the shortest distance. Then, the optimization processor 212 outputs the first estimated thickness 308 (S212).

Next, the optimization processor 212 executes the second search to search in the second search direction 305b for a point where the likelihood becomes the highest (second estimated thickness (second value) 309), with the shifted starting point 304 as a starting point (S213). In the example in FIG. 4, the second estimated thickness 309 is a combination of the thickness of the first base material and the thickness of the second base material. As a result, the second estimated thickness 309 is outputted (S214). The procedure of the second search is the same as that of the first search.

As described above, the optimization processor 212 sets the shifted starting point 304, which is slightly shifted toward the ridge structure representative line 321 from the estimated thickness input value 301. The shifted amount is a width about the substance resolution bandwidth predicted from the X-ray dose during radiation, for example. The optimization processor 212 then executes the second search in the second search direction 305b, parallel to the first search direction 305a, with the shifted starting point 304 as a starting point. This allows the optimization processor 212 to acquire the second estimated thickness 309, which is a point on the ridge of the likelihood contours 300, at the shortest distance, as with the first search. Note that the second search is required to have a different starting point or search direction from the first search, and is desirably executed in the direction perpendicular to the ridge structure representative line 321, with the shifted starting point 304, which is slightly shifted from the estimated thickness input value 301 along the ridge structure representative line 321, as a starting point, as shown in FIG. 4.

A straight line connecting the two points of the first estimated thickness 308 and the second estimated thickness 309 with each other is expected to correspond to the straight ridge structure of the likelihood contours 300, as shown in FIG. 4. The optimization processor 212 sets this direction as a third search direction 310 (S221). The optimization processor 212 then executes the third search of searching in the third search direction 310 for a point, where the likelihood becomes the highest (S222). Note that there are two third search directions 310 (those indicated by reference numerals 310a and 310b in FIG. 4). However, the magnitude of the likelihood is known at the first estimated thickness 308 and the second estimated thickness 309, and thus the direction having the increasing likelihood may be selected as the third search direction 310. In addition, the optimization processor 212 selects the larger one of the first estimated thickness 308 and the second estimated thickness 309 (the second estimated thickness 309 in the case of FIG. 4) as the starting point of the third search. As described above, searching by the third search ideally obtains the highest likelihood estimator of the entire space in the coordinate space, in the ridge direction, of the likelihood contours 300. The optimization processor 212 outputs the point having the highest likelihood in the third search direction 310 as an estimated thickness output value (estimated parameter value) 312 (S223). In the example in FIG. 4, the estimated thickness output value 312 is a combination of the thickness of the first base material and the thickness of the second base material.

Then, the projection-based processor 211 generates the estimated base material thickness projection data 241 (see FIG. 3), based on the estimated thickness output value 312 outputted as above.

If the estimated thickness input value 301 is completely unknown, the shifted starting point 304 may be substantially shifted. Besides, this operation (ridge search method) may be repeated as required, using the estimated thickness output value 312 as the new estimated thickness input value 301 (broken arrow in FIG. 5). Repeating the optimization process in this way improves the solution in a step-by-step manner.

The present embodiment uses an optimization method by a ridge search method specialized for the case where distribution of the likelihood forms a linear structure. This allows for significantly reducing the number of iterations of the high load calculation of the likelihood. In addition, the first and second searches in the present embodiment are executed in a direction perpendicular to the ridge line in planar view of the likelihood contours 300. This allows for searching the first estimated thickness 308 and the second estimated thickness 309 with the shortest distance (that is, the lowest load) from the estimated thickness input value 301 and the shifted starting point 304.

Further, the optimization processor 212 in the present embodiment sets the shifted starting point 304 at a location away from the estimated thickness input value 301 by a predetermined distance along the ridge line of the likelihood contours 300. This allows for shortening the search distance of the second search to reduce the calculation load.

Note that the present embodiment assumes Photo Counting CT (PCCT) or spectral CT, but the technique of the present embodiment may be applied to Dual Energy CT. In this case, base material energy shall be used instead of the thickness of the base material.

The present invention is not limited to the above-described embodiment, and includes various modifications. The above-described embodiment has been described in detail for the purpose of illustrating the present invention, and is not necessarily limited to having all the configurations as described.

In addition, each of the above-described configurations, functions, processors 211 to 214, the storage unit 23, and the like may partly or entirely be implemented by hardware, such as with being designed into an integrated circuit. Alternatively, as shown in FIG. 2, the above-described configurations, functions, and the like may be implemented by software, with a processor such as the CPU 22 interpreting and executing programs to implement respective functions. Information such as programs, tables, and files for implementing respective functions may be stored in the memory 21, a recording device such as an SSD (Solid State Drive), or a recording medium such as an IC (Integrated Circuit) card, an SD (Secure Digital) card and a DVD (Digital Versatile Disc), other than being stored in the HD. In the present embodiment, control lines and information lines are those considered necessary for the purpose of illustration, and not all control lines and information lines in the product are necessarily shown. In practice, it is safe to consider that almost all components are connected to one another.

LIST OF REFERENCE SIGNS

1: X-ray CT device, 2: computing device (computing unit), 3: input device, 4: display device, 10: X-ray CT system, 211: projection-based processor, 212: optimization processor, 213: image reconstruction processor, 214: display processor, 231: ridge structure representative angle, 232: measured spectrum projection data, 300: likelihood contours, 301: estimated thickness input value (predetermined parameter), 302: actual ridge structure angle, 304: shifted starting point, 305a: first search direction, 305b: second search direction, 308: first estimated thickness (first value), 309: second estimated thickness (second value), 310: third search direction, 312: estimated thickness output value (estimated parameter value), and 321: ridge structure representative line.

The invention claimed is:

1. A parameter estimation method for an X-ray CT (Computer Tomography) system, the method comprising:
providing the X-ray CT system comprising an X-ray CT device with an x-ray tube and an x-ray detector and a computing unit with an input unit, a processor and a trans receiver;
irradiating an imaged subject using X-rays generated by the X-ray tube;
measuring X-rays attenuated by the imaged subject with the X-ray detector;
receiving the data from the X-ray detector;
applying a projection-based method to X-ray attenuation responses from the received data by using the computing unit, wherein the X-ray attenuation responses having X-ray energy distribution for an N, where N≥2, number of first parameters;
reconstructing an image with the computing unit by using estimated values on given values in the X-ray attenuation responses for an M, M≤N, number of second parameters, parameters, the second parameters being based materials;

setting a coordinate space to have coordinate axes that represent the M number of second parameters and a likelihood of the M number of second parameters;

executing a first step of setting a predetermined starting point in the coordinate space based on the X-ray attenuation responses, and doing a first search to search in a predetermined direction in the coordinate space from the predetermined starting point for a first value to have a highest likelihood;

executing a second step of doing a second search to search for a second value to have the highest likelihood, under the condition that at least one of a starting point and a direction for the second search is different from that for the first search; and executing a third step of doing a third search to search on a line connecting the first value with the second value for a highest likelihood estimator to have the highest likelihood, and setting the highest likelihood estimator as an estimated value by the M number of second parameters, wherein an angle formed by a ridge line with respect to one of the coordinate axes in a distribution of the likelihood with respect to one of the coordinate axes of the M number of second parameters in the coordinate space is input through an input unit, and wherein the first and second searches in the first and second steps are executed in a direction perpendicular to the ridge line.

2. The parameter estimation method as claimed in claim 1, wherein the predetermined starting point for the second search is set to a location away from the starting point for the first search by a predetermined distance in a direction parallel to the ridge line.

3. An X-ray CT (Computer Tomography) system comprising:

an X-ray CT device comprising an x-ray tube and an x-ray detector, the X-ray tube irradiates X-rays and the X-rays irradiated by the X-ray tube and attenuated by an imaged subject are measured by the X-ray detector;

a computing unit comprising a processor, an input unit, and a transceiver coupled to the processor, the transceiver configured to receive data from the X-ray detector which includes X-ray attenuation responses through the imaged subject, having X-ray energy distribution for an N, where N≥2, number of first parameters, for obtaining an N number of projection data, wherein the computing unit is configured to:

apply a projection-based method to the projection data, to reconstruct an image using estimated values on given values in the X-ray attenuation responses for an M, where M≤N, number of second parameters, set a coordinate space to have coordinate axes that represent the M number of second parameters and a likelihood of the M number of second parameters, and execute:

a first step of setting a predetermined starting point in the coordinate space based on the X-ray attenuation responses, and doing a first search to search in a predetermined direction in the coordinate space from the predetermined starting point for a first value to have a highest likelihood;

a second step of doing a second search to search for a second value to have the highest likelihood, under the condition that at least one of a starting point and a direction for the second search is different from that for the first search; and a third step of doing a third search to search on a line connecting the first value with the second value for a highest likelihood estimator to have the highest likelihood, and setting the highest likelihood estimator as an estimated value by the M number of second parameters, wherein an angle formed by a ridge line with respect to one of the coordinate axes in a distribution of the likelihood with respect to one of the coordinate axes of the M number of second parameters in the coordinate space is inputted through the input unit, and wherein the first and second searches in the first and second steps are executed in a direction perpendicular to the ridge line.

4. The X-ray CT system as claimed in claim 3, wherein the predetermined starting point for the second search is set to a location away from the starting point for the first search by a predetermined distance in a direction parallel to the ridge line.

* * * * *